United States Patent [19]
Koike et al.

[11] 4,057,555
[45] Nov. 8, 1977

[54] PROCESS FOR PRODUCING SACCHARIN

[75] Inventors: Wataro Koike; Takahiro Kimoto, both of Shizuoka; Sadayoshi Matsui, Shimizu, all of Japan

[73] Assignee: Ihara Chemical Industry Co., Ltd., Tokyo, Japan

[21] Appl. No.: 677,256

[22] Filed: Apr. 15, 1976

[30] Foreign Application Priority Data

Dec. 6, 1975 Japan ............................. 50-145246
June 11, 1975 Japan ............................. 50-70311

[51] Int. Cl.² .......................................... C07D 275/06
[52] U.S. Cl. .............................. 260/301; 260/327 S; 260/507 R; 260/544 S; 560/17; 560/14; 560/12
[58] Field of Search .......................................... 260/301

[56] References Cited
U.S. PATENT DOCUMENTS 564,784   7/1896   Fahlberg ............................. 260/301

Primary Examiner—R. Gallagher
Attorney, Agent, or Firm—Oblon, Fisher, Spivak, McClelland & Maier

[57] ABSTRACT 1,2-Benzoisothiazole-3-on-1,1-dioxide having the formula

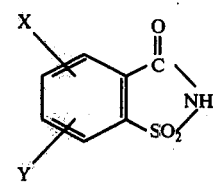

wherein X represents hydrogen, halogen, nitro, lower alkyl or lower alkoxy and Y represents hydrogen, halogen, lower alkyl, or lower alkoxy is prepared by reacting phosgene with an o-sulfobenzoic acid compound having the formula:

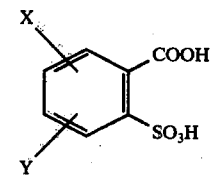

or an alkali metal salt or alkaline earth metal salt thereof in the presence of dimethylformamide, thereby producing a mixture of a dichlorotolylsultone and a chlorosulfonylbenzoylchloride; (b) reacting the reaction products of step (a) with an alcohol of the formula ROH wherein R represents a lower alkyl group; and then (c) reacting the product of step (b) with ammonia.

11 Claims, No Drawings

PROCESS FOR PRODUCING SACCHARIN

BACKGROUND OF THE INVENTION:

1. Field of the Invention:

The present invention relates to a new process for producing 1.2-benzoisothiazole-3-on-1.1-dioxide (saccharine derivatives) which is useful as a medicinal agent (sweetener for diabectics) food additives sweetener and as an intermediate for agricultural chemicals such as germicides to obtain hygienically nontoxic products. More particularly, the invention relates to a process for producing 1.2-benzoisothiazole-3-on-1.1-dioxides possesing high purity in high yield without contamination by toluenesulfonamide which may be hygienically toxic, by a sequence of new reaction steps from o-sulfobenzoic acid.

2. Description of the Prior Art:

It is known that 1.2-benzoisothiazole-3-on1.1-dioxides can be produced by the reactions of Reaction scheme (1) in which the first steps in the chlorosulfonation of toluene; the second step is the separation and purification of o-toluenesulfochloride and p-toluenesulfochloride which are produced in the first step the; third is the reaction of the o-toluenesulfochloride separated and purified in the second step with ammonia; and fourth step is the oxidation of o-toluenesulfonamide produced in the third step with a solution of bichromate in concentrated sulfuric acid J. Am. Chem. Soc. Vol. 1. page 426, 1879; BP 174, 913 and BP 682.800).

REACTION SCHEME (1):

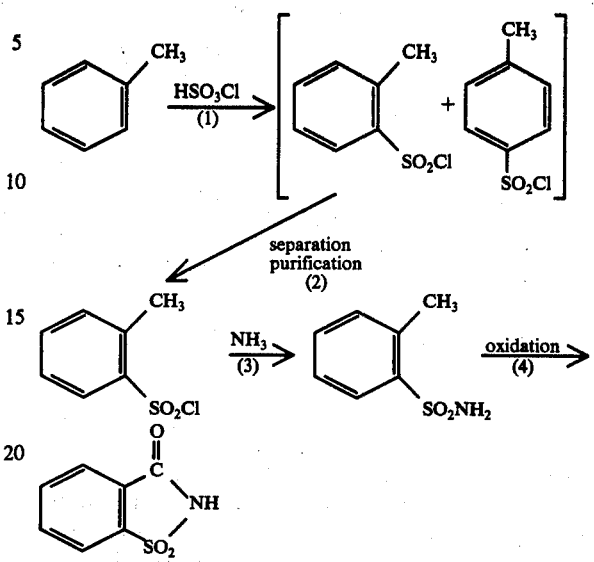

It is also known that 1.2-benzoisothiazole-3-on-1.1dioxide can be produced by the reactions of Reaction scheme (2) in which the first step is the reaction of phthalic anhydride with ammonia, the second step is the Hoffmann reaction of the phthalimide produced in the first step; the third step is the diazotation of the o-aminobenzoic acid produced in the second step; the fourth step the reaction of sodium sulfide with the diazobenzoic acid produced in the third step the fifth step is the treatment of the sodium dithiodibenzoate produced in the fourth step with an acid; the sixth step is the methyl-esterification of the dithiodibenzoic acid produced in the fifth step; the seventh step is the reaction of the dimethyl dithiodibenzoate produced in the sixth step with chlorine; and the eighth step is the reaction of the methyl o-sulfochlorobenzoate produced in the seventh step with ammonia (Chemical Engineering, Vol. 61, No. 7 page 128, 1954).

REACTION SCHEME (2):

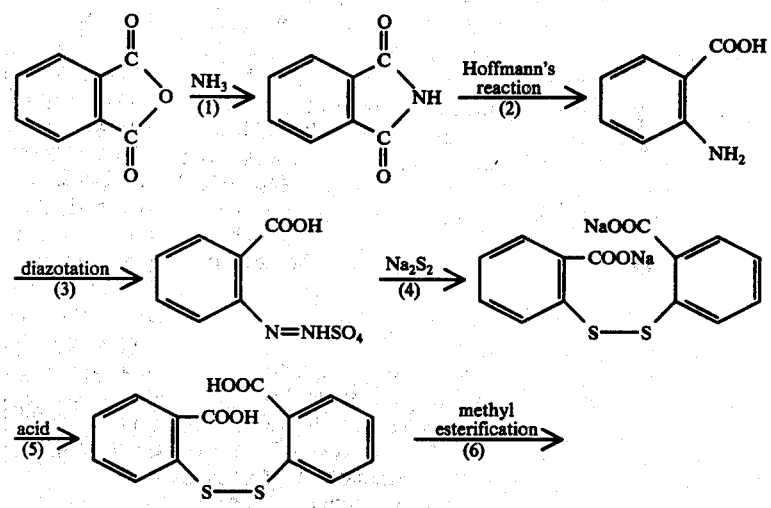

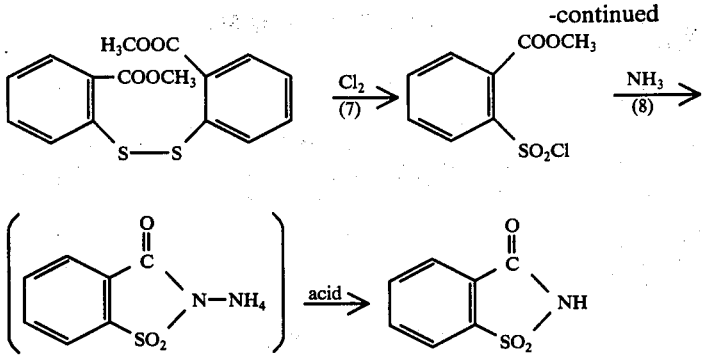

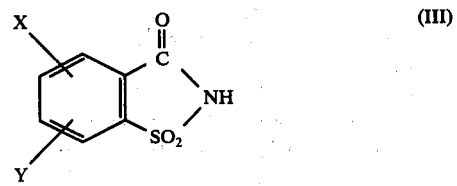

In the conventional process of Reaction scheme (1) which employs toluene, as a reactant a large amount of p-toluene-sulfochloride is produced as a by-product together with o-toluenesulfochloride in the first step. Accordingly, the separation and purification procedure of the second step is quite troublesome. That is, the reaction mixture formed in the first step must be poured into water to precipitate crystals of p-toluenesulfochloride and the crystals are centrifugally separated. The remaining oily product of o-toluenesulfochloride is further cooled to precipitate crystals of p-toluenesulfochloride, and the operation is repeated. However, it is difficult to separate all of the p-toluenesulfochloride from the oily o-toluenesulfochloride. Consequently, it is necessary to separate p-toluenesulfonamide as a by-product after the reaction with ammonia in the third step. Moreover, it is necessary to treat a large amount of the waste bichromate conc. sulfuric acid mixture used in the oxidation reaction of the fourth step. In order to recover and reuse chromium oxide formed from the bichromate, it is necessary to use a large electrolyzer. Moreover, another serious disadvantage of the conventional process is the fact that both o-toluenesulfonamide and p-toluenesulfonamide are believed to cause cancer. For these reasons, in the conventional process, it is necessary to separate the toxic compounds to purify the product. If the toxic compounds remain with the 1.2-benzoisothiazole-3-on-1.1-dioxide when it is used as a food additive, there is the possibility that it will adversely effect the human body. Accordingly, the conventional process is not a hygienically safe process. In the conventional process of the Reaction scheme (2) which was phthalic anhydride as the starting material, it is necessary to use a full eight step process. Consequently, the scheme is complicated and it is hard to achieve high yields of 1.2-benzoisothiazole-3-on-1.1-dioxide such as about 50 % based on the phthalic anhydride used as the starting material. None of the known processes are satisfactory as industrial methods.

SUMMARY OF THE INVENTION

One object of the present invention is to provide a process for producing 1.2-benzoisothiazole-3-on-1.1-dioxides in high yield free of contaminating toluenesulfonamide which may be toxic. This object and other objects of the invention have been attained by providing a process for producing 1.2-benzoisothiazole-3-on-1.1-dioxides having the formula

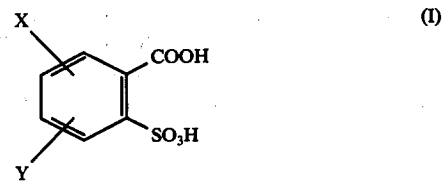

wherein X represents hydrogen halogen, nitro lower alkyl or lower alkoxy and Y represents hydrogen, halogen a lower alkyl or a lower alkoxy by reacting phosgene with an o-sulfobenzoic acid having the formula or an alkali metal salt or alkaline earth metal salt thereof, in the presence of dimethylformamide; reacting the reaction product with an alcohol having the formula R—OH (II), wherein R represents a lower alkyl group; and then reacting ammonia with the resulting reaction product.

DETAILED DESCRIPTION OF THE PREFERRED EMBODIMENTS:

Various processes for producing 1.2-benzoisothiazole-3-on-1.1-dioxides have been studied. As the result, it has been foundthat both the carboxylic group and the sulfonic acid group bonded to o-sulfobenzoic acid can be simultaneously chlorinated by reacting phosgene with an o-sulfobenzoic acid, an alkali metal salt thereof or alkaline earth metal salt in the presence of dimethylformamide, whereby a mixture of o-chlorosulfonylbenzoylchloride and dichlorotolylsultone is produced, thereafter, o-chlorosulfonylbenzoylchloride is esterified by reacting the resultant mixture with an alcohol 1.2-Benzoisothiazole-3-on-1.1-dioxide is produced as the single product by reacting ammonia with the esterified mixture. In the reaction scheme (1) of the invention, as shown by the following reaction dimethylformamide reacts with phosgene, and the reaction product (a) is used as the chlorinating agent for the aromatic sulfocarboxylic acid (b), or an alkali metal salt derivative thereof [(c), (d) and (e)] or an alkaline earth metal thereof [(f) (g) and (h)], whereby the chlorination reaction is conducted as shown in reaction scheme (ii) to produce a mixture of chlorosulfonylbenzoylchloride (1 V) and dichlorotolylsultone (V). Dimethylformamide is recovered from the reaction. As shown by Reaction scheme (iii), chlorosulfonylbenzoylchloride (IV) in the mixture is esterified by reacting the alcohol (II) with the mixture of chlorosulfonylbenzoylchloride (IV) and dichlorotolylsultone (V) to produce the alkyl chlorosulfonylbenzoate (VI). Both compound (VI) and compound (V) are converted to the desired 1.2-benzothiazole-3-on-1.1-dioxide product by reacting the mixture of compound (VI) and compound (V) with ammonia.

REACTION SCHEME (i)

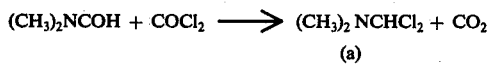
(a)

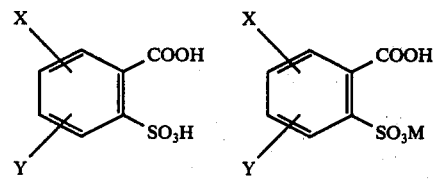

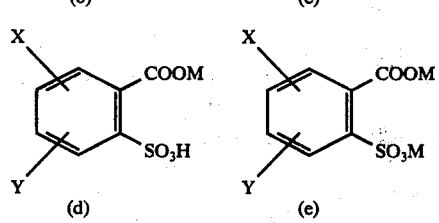

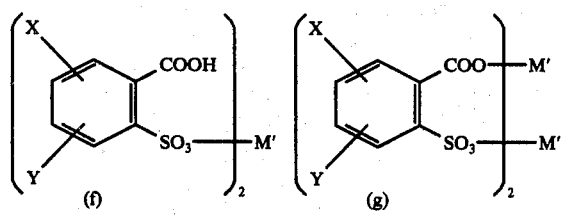

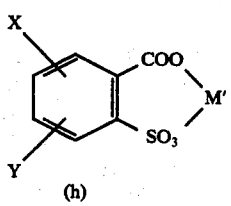
(h)

REACTION SCHEME (ii)

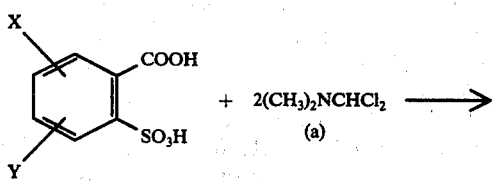
(a)

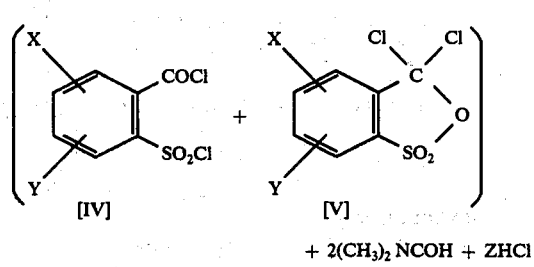

+ 2(CH₃)₂NCOH + ZHCl

REACTION SCHEME (ii)

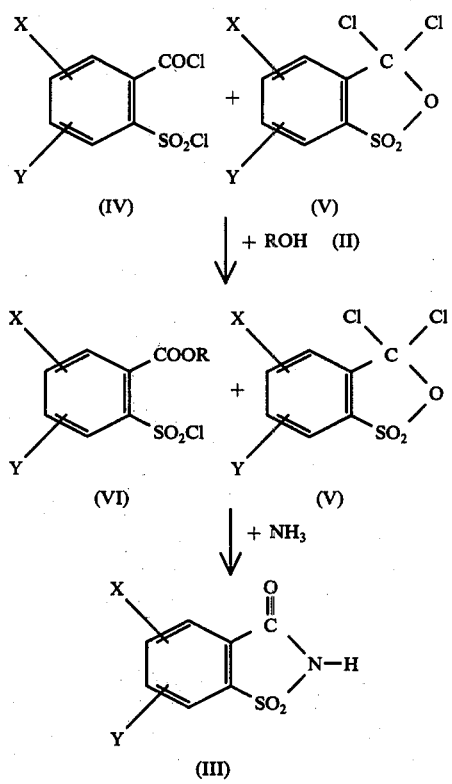

In all of the reaction schemes above, X and Y are as defined above, M is an alkali metal and M' is an alkaline earth metal.

In the process of the invention, an o-sulfonylbenzoic acid of formula (I) or an alkali metal salt or alkaline earth metal salt therefore is used. In formula (I), X and Y can be bonded at any desired position on the benzene ring, and X can be hydrogen halogen, nitro, lower alkyl or lower alkoxy and Y can be hydrogen, halogen, lower alkyl or lower alkoxy. The scope of the term halogen atom includes chlorine, bromine, iodine and fluorine. Suitable lower alkyl groups include methyl, ethyl, n-propyl, iso-propyl n-butyl, iso-butyl or tert-butyl. Suitable lower alkoxy groups include methoxy, ethoxy, n-propoxy, iso-propoxy, n-butoxy, iso-butoxy, and tert-butoxy.

The alkali metal salts or alkaline earth metal salts of the o-sulfobenzoic acid having formula (I), can be the alkali metal salts (c), (d) and (e) and the alkaline earth metal salts (f), (g) and (h) or mixtures thereof. Suitable alkali metals include sodium, potassium and suitable the like and alkaline earth metals include magnesium, calcium, barium and the like.

The o-sulfobenzoic acid (I) can be produced by the oxidation of toluenesulfonic acid or the sulfonation of an aromatic carboxylic acid. The monometal salts (c) and (f) can be prepared by salting out the corresponding o-sulfobenzoic acid (I). The dimetal salts (e), (g) and (h) can be prepared by neutralizing the corresponding o-sulfobenzoic acid (I) with an alkali metal hydroxide or an alkaline earth metal hydroxide.

The process of the invention includes a first step of reaching phosgene with the o-sulfobenzoic acid (I) or an alkali metal salt or alkaline earth metal salt thereof in the presence of dimethylformamide; a second step of reacting the alcohol with the reaction product of the first step; and a third step of reaching ammonia with the reaction product of the second step. The reaction of phosgene with an o-sulfobenzoic acid (I) or the alkali metal salt or alkaline earth metal salt thereof in the presence of dimethylformamide in the first step can be usually conducted in an inert organic solvent. The amount of dimethylformamide used in the reaction is in a range of less than 1 mole, usually 0.01 - 0.3 mole, preferably 0.03 - 0.1 mole per mole of the o-sulfobenzoic acid, or the alkali metal salt or alkaline earth metal salt thereof. It is possible to use an excess amount of dimethylformamide, in the reaction, although it is not economical to do so. Phosgene can be used in amounts greater than equivalent amounts preferably 5 - 20 % in excess. Phosgen can be directly introduced into the reaction system or it can also be used by dissolving it in an inert organic solvent such as carbon tetrachloride, toluene or the like. Suitable inert organic solvents used in the reaction include aliphatic hydrocarbons such as cyclohexane, n-hexane and the like; halohydrocarbons such as chloroform, carbon tetrachloride, trichloroethylene, tetrachloroethylene and the like; aromatic hydrocarbons such as benzene, toluene, xylene, chlorobenzene and the like; ethers such as diethyl ether, dibutyl ether, dioxane and the like; ketones such as acetone, methylethyl ketone, methylisopropyl ketone and the like; nitriles such acetonitrile, propionitrile and the like and esters such as ethyl acetate, butyl acetate and the like. The reaction temperature and the reaction time are selected depending upon type of the aromatic sulfocarboxylic acid used, or alkali metal salt or alkaline earth metal salt thereof and the rate at which is fed. The reaction temperature is usually in a range of 20° - 150° C, preferably 40° -100° C. The reaction time can be less than 8 hours and is usually in a range of 5 - 7 hours.

In the second step of the reaction of the alcohol (II) with the reaction mixture produced in the first step, it is possible to directly react the alcohol with the reaction mixture without any treatment after the first step. Thus, it is possible to react the alcohol with the condensed reaction product which is produced by removing the inert organic solvent from the reaction mixture after the first step by distillation. Suitable alcohols (II) used in the reaction are preferably lower alcohols such as methanol, ethanol, n-propanol, n-butanol and the like. The amount of alcohol employed is usually in a range of 0.5 - 8.0 mole, preferably 1.0 - 5.0 mole per mole of the o-sulfobenzoic acid (I) or the alkali metal salt or alkaline earth metal salt thereof. The reaction temperature is in a range of 5° - 40° C preferably 15° - 30° C. The reaction time can be less than two hours and usually is in a range of 0.5 - 1 hour.

In the third step the reaction of ammonia is reacted with the reaction product produced in the second step. It is possible to react the components by injecting ammonia into the reaction mixture after the second step. Thus, it is preferable to react ammonia and the second step product by mixing an aqueous solution of ammonia with the reaction mixture after the second step. The amount of ammonia employed is preferably in a range of 3.5 - 4.5 mole per mole of the o-sulfobenzoic acid (I) or the alkali metal salt or alkaline earth metal salt thereof. Preferably, a 4 - 28 % of an aqueous solution of ammonia is used. The reaction temperature is usually in the range of 5° - 35° C, and if desired, the reaction is conducted while cooled. After the reaction with ammonia, the ammonium salt of 1.2-benzoisothiazole-3-on-1.1-dioxide (III) is obtained. The desired compound, i.e. 1.2-benzoisothiazole-3-on-1.1-dioxide (III) can be separated by precipitation by treating the solution with a mineral acid such as hydrochloric acid, sulfuric acid, nitric acid, phosphoric acid or the like. In accordance with the process of the invention, the desired 1.2-benzoisothiazole-3-on-1.1-dioxide compound (III) having high purity can be easily produced in substantial industrial efficiency in yields greater than 80 % based on the o-sulfobenzoic acid.

The positions of the substituents in the 1.2-benzoisothiazole-3-on-1.1-dioxides compounds (III) can be shown as follows.

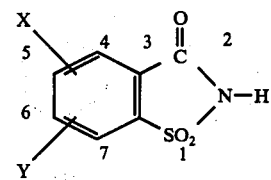

Suitable 1.2-benzoisothiazole-3-on-1.1-dioxides (III) produced by the process of the invention include 1.2-benzoisothiazole-3-on-1.1-dioxide, 6-fluoro-1.2-benzoisothiazole-3-on-1.1-dioxide, 6-chloro1.2-benzoisothiazole-3-on-1.1-dioxide, 6-bromo-1.2-benzoisothiazole3-on-1.1-dioxide, 6-iodo-1.2-benzoisothiazole-3-on-1.1-dioxide, 5.6-dichloro-1.2-benzoisothiazole-3-on-1.1-dioxide, 5-nitro-1.2-benzoisothiazole-3-on-1.1-dioxide, 6-nitro-1.2-benzoisothiazole-3-on-1.1-dioxide, 6-methyl-1.2-benzoisothiazole-3-on-1.1-dioxide, 5.7-dimethyl-1.2-benzoisothiazole-3-on-1.1-dioxide, 5-methyl-6-nitro1.2-benzoisothiazole-3-on-1.1-dioxide, 6-methoxy-1.2-benzoisothiazole3-on-1.1-dioxide, 5.6-dimethoxy-1.2-benzoisothiazole-3-on-1.1-dioxide, 6-ethoxy-1.2-benzoisothiazole-3-on-1.1-dioxide and the like.

The characteristics and advantages of the process of the invention will now be enumerated.

1. The reaction steps are short. The desired of 1.2benzoisothiazole-3-on-1.1-dioxide compounds (III) can be continuously produced in high yield from o-sulfobenzoic acids without separating the intermediates from the reaction to effect purification without complicated operations.

2. The desired 1.2-benzoisothiazole-3-on-1.1-dioxide compounds (III) can be produced in high purity without contaminating amounts of toluenesulfonamide which may be toxic to the human body. Consequently, the 1.2-benzoisothiazole-3-on-1.1-dioxide can be used safely as a sweetner for human beings.

3. The chlorosulfonylbenzoylchlorides as intermediates have been conventionaly produced by chlorinating the alkali metal salt or ammonium salt of sulfobenzoic acid with a mixture of phosphorus pentachloride and phosphorus oxychloride or chlorosulfonating benzoic acid and then chlorinating it with thionyl chloride. These processes are quite complicated. On the contrary, in the first step of the present process, both the carboxyl group and the sulfonic acid group of the o-sulfobenzoic acid can be simultaneously chlorinated under mild conditions.

The invention will be further illustrated by certain examples.

EXAMPLE 1

Preparation of 1.2-benzoisothiazole-3-on-1.1-dioxide

First step:

In a four necked flask equipped with a stirrer, a thermometer, a condenser and a dropping funnel, 20.2 g (0.1 mole) of o-sulfobenzoic acid, 75 ml of carbon tetrachloride and 0.22 g (0.003 mole) of dimethylformamide were charged. The mixture was stirred at 70° -75° C and 75 ml of carbon tetrachloride solution of phosgene (phosgene content of 30% WV: 0.22 mole) were added dropwise and the mixture was reacted for 7 hours. After the reaction, nitrogen gas was injected to remove excess phosgene.

Second step:

In a three necked flask equipped with a stirrer, and a thermometer, 12.8 g (0.4 mole) of methanol were charged and all the reaction mixture obtained in the first step was added to the methanol solution and the resulting mixture was reacted with stirred at 15° C for 1 hour.

Third step:

In a four necked flask equipped with a stirrer, a thermometer, a condenser and a dropping funnel, 90 g (0.42 mole) of an 8 % aqueous solution of ammonia was charged. The reaction mixture produced in the second step was added dropwise to the aqueous solution of ammonia at 15° - 20° C with stirring and the reaction was continued for 4 hours. After the reaction, the organic phase was separated from the aqueous solution phase, and 6N - HCl was added dropwise to the aqueous solution phase with stirring to adjust the pH to 1. The precipitated crystals were filtered and washed with 30 ml of water and dried whereby 15.1 g of white crystals of 1.2-benzoisothiazole3-on-1.1-dioxide having a melting point of 227° - 229° C (yield of 82.4 % o-sulfobenzoic acid were obtained. The purity of the resulting 1.2-benzoisothiazole-3-on-1.1-dioxide was 99.8% by neutralization titration analysis.

EXAMPLE 2

Preparation of 1.2-benzoisothiazole-3-on 1.1-dioxide

First step 1:

Into a four necked flask equipped with a stirrer, a thermometer, a condenser and a phosgene inlet, were charged 24.0 g (0.1 mole) of the monopotassium salt of o-sulfobenzoic acid

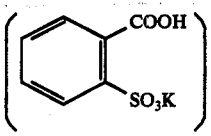

150 ml of toluene and 0.22 g (0.003 mole) of dimethylformamide. The mixture was stirred at 80° C and 23 g of phosgene were introduced into the mixture over 4 hours. The reaction was continued by maintaining the temperature at 80° - 90° C under refluxing with stirring for 3 hours. After the reaction, nitrogen gas was injected into the mixture to remove excess phosgene. The reaction mixture was filtered to remove potassium chloride and the filtrate was condensed and a colorless condensate was obtained.

Second step:

Into a three necked flask equipped with a stirrer and a thermometer, was charged 13.8 g (0.3 mole) of ethanol. The condensate produced in the first step was also charged. The reaction was continued with stirring at 10° C for 1 hour.

Third step:

Into a four-necked flask equipped with a stirrer, a thermometer, a condenser, and a dropping funnel, was charged 71.0 g (0.42 mole) of a 10 % aqueous solution of ammonia. The reaction mixture produced in the second step was added dropwise to the aqueous solution of ammonia at 15° - 20° C with stirring and the reaction was continued for 4 hours. After the reaction, 6N - HCl was added dropwise to the reaction mixture with stirring to adjust the pH to 1. The precipitated crystals were filtered and washed with 30 ml of water and dried whereby 16.0 g of white crystals of 1.2-benzoisothiazole-3-on-1.1-dioxide having a melting point of 228° -229° C (yield of 87.3 % based on o-sulfobenzoic acid) were obtained.

EXAMPLE 3:

In accordance with the process of Example 2, phosgene was introduced into several solutions each containing on o-sulfobenzoic acid (i) or an alkali metal salt or alkaline earth metal salt thereof an inert organic solvent in the presence of dimethylformamide as the first step, and an alcohol was added to each solution and reacted in the second step an aqueous solution of ammonia was added to each solution and reacted in as the third step. The product was precipitated by adding hydrochloric acid to each solution whereby various 1.2-benzoisothiazole-3-on-1.1-dioxide compounds were obtained. The conditions of the first, second and third steps are shown in Table 1 and the results are shown in Table 2.

Table 1

| Experiment No. | Starting material (Amount (g)) | First step Amount of dimethyl formamide(g) | Solvent Amount (ml) | Amount of phosgene (g) | Reaction Conditions Temp. (° C) | Time (hr) |
|---|---|---|---|---|---|---|
| 1 | 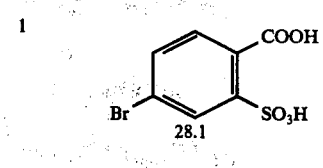 28.1 | 0.25 | chlorobenzene 120 | 22.0 | 90 | 7 |

Table 1-continued

| Experiment No. | Starting material (Amount (g)) | First step Amount of dimethyl formamide(g) | Solvent Amount (ml) | Amount of phosgene (g) | Reaction Conditions Temp. (°C) | Time (hr) |
|---|---|---|---|---|---|---|
| 2 | 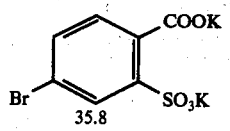 Br— (COOK, SO₃K) 35.8 | 0.25 | xylene 120 | 23.0 | 90 | 7 |
| 3 | 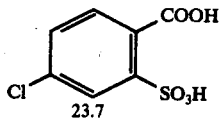 Cl— (COOH, SO₃H) 23.7 | 0.22 | carbon-tetra-chloride 120 | 23.0 | 75 | 7 |
| 4 | 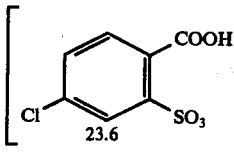 [Cl—(COOH, SO₃)]₂Ba 23.6 | 0.25 | chloro-benzene 120 | 23.5 | 95 | 7 |
| 5 | 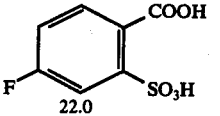 F— (COOH, SO₃H) 22.0 | 0.25 | toluene 120 | 22.0 | 90 | 7 |
| 6 | 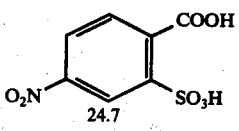 O₂N— (COOH, SO₃H) 24.7 | 0.22 | tetra-chloro-ethylene 120 | 22.0 | 90 | 7 |
| 7 | 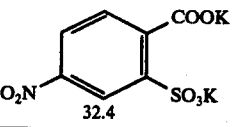 O₂N— (COOK, SO₃K) 32.4 | 0.30 | isopropyl methyl-ethyl-ketone 120 | 22.0 | 80 | 7 |

Table 1'

| Experiment No. | Second step ROH (II) Amount (g) | Reaction Temp. (°C) | Time (hr) | Third step Amount of 10% NH₃aq | Reaction Conditions Temp. (°C) | Time (hr) |
|---|---|---|---|---|---|---|
| 1 | methanol 12.8 | 15 | 1 | 70 | 20 | 4 |
| 2 | methanol 16.0 | 15 | 1 | 70 | 20 | 4 |
| 3 | ethanol 18.4 | 15 | 1 | 70 | 20 | 4 |
| 4 | methanol 15.0 | 15 | 1 | 70 | 20 | 4 |
| 5 | n-propanol 24.0 | 15 | 1 | 70 | 20 | 4 |
| 6 | ethanol 17.0 | 15 | 1 | 70 | 20 | 4 |
| 7 | methanol 15.0 | 15 | 1 | 70 | 20 | 4 |

Table 1"

| Experiment No. | Product | Melting point °C | Amount (g) | Yield % |
|---|---|---|---|---|
| 1 | 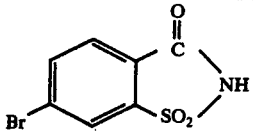 | 215–217 | 21.5 | 82.0 |
| 2 | 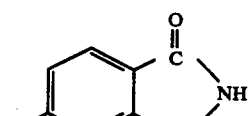 | 215–217 | 22.0 | 83.9 |
| 3 | 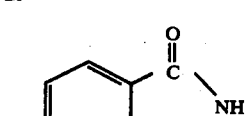 | 216–218 | 18.0 | 82.7 |
| 4 | 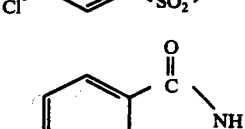 | 216–218 | 17.7 | 81.3 |

Table 1"-continued

| Experiment No. | Product | Melting point °C | Amount (g) | Yield % |
|---|---|---|---|---|
| 5 | 4-fluoro benzene with C(=O)-NH-SO₂ ring (F substituent) | 200-202 | 16.6 | 82.5 |
| 6 | benzene with C(=O)-NH-SO₂ ring, O₂N substituent | 207-209 | 19.3 | 84.6 |
| 7 | benzene with C(=O)-NH-SO₂ ring, O₂N substituent (isomer) | 207-209 | 19.0 | 83.3 |

Table 2'

| Experiment No. | Second step ROH (II) Amount (g) | Second step Reaction Conditions Temp. (°C) | Second step Reaction Conditions Time (hr) | Amount of 10% NH₃aq | Third step Reaction Conditions Temp. (°C) | Third step Reaction Conditions Time (hr) |
|---|---|---|---|---|---|---|
| 8 | n-butanol 22.2 | 20 | 1 | 70 | 20 | 4 |
| 9 | methanol 15.0 | 20 | 1 | 70 | 20 | 4 |
| 10 | ethanol 16.0 | 20 | 1 | 70 | 20 | 4 |
| 11 | ethanol 16.0 | 20 | 1 | 70 | 20 | 4 |
| 12 | methanol 15.0 | 20 | 1 | 70 | 20 | 4 |
| 13 | methanol 15.0 | 20 | 1 | 70 | 20 | 4 |

Table 2

| Experiment No. | Starting material (Amount (g)) | First step Amount of dimethyl formamide (g) | Solvent Amount (ml) | Amount of phosgene (g) | Reaction Conditions Temp. (°C) | Reaction Conditions Time (hr) |
|---|---|---|---|---|---|---|
| 8 | 4-methyl-2-(SO₃K)-benzoic acid 25.4 | 0.22 | acetonitrile 120 | 23.0 | 75 | 7 |
| 9 | 3,5-dimethyl-2-(SO₃H)-benzoic acid 23.0 | 0.30 | carbon-tetrachloride 120 | 23.0 | 75 | 7 |
| 10 | 4-methyl-5-nitro-2-(SO₃K)-benzoic acid 29.9 | 0.30 | chlorobenzene 120 | 23.0 | 80 | 7 |
| 11 | 4-methoxy-2-(SO₃H)-benzoic acid 27.0 | 0.30 | xylene 120 | 23.0 | 85 | 7 |
| 12 | 4-ethoxy-2-(SO₃H)-benzoic acid 24.6 | 0.40 | toluene 120 | 22.0 | 80 | 7 |
| 13 | 4,5-dimethoxy-2-(SO₃K)-benzoic acid 30.0 | 0.40 | chlorobenzene 120 | 22.0 | 85 | 7 |

Table 2"

| Experiment No. | Product | Melting point °C | Amount (g) | Yield % |
|---|---|---|---|---|
| 8 | | 247–249 | 17.1 | 86.7 |
| 9 | | 261–263 | 17.5 | 82.8 |
| 10 | | 211–213 | 20.0 | 82.6 |
| 11 | | 269–271 | 18.4 | 86.3 |
| 12 | | 257–258 | 19.2 | 84.5 |
| 13 | | 278–290 | 20.0 | 83.0 |

We claim:
1. A process for producing 1.2-benzoisothiazole3-on-1.1-dioxide having the formula:

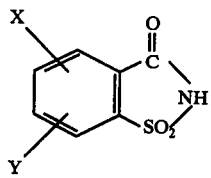

wherein X represents hydrogen, halogen, nitro, lower alkyl or lower alkoxy and Y represents hydrogen, halogen, lower alkyl, or lower alkoxy which comprises: (a) reacting phosgene with an o-sulfobenzoic acid compound having the formula:

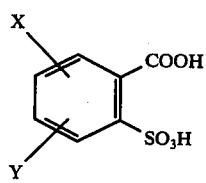

or an alkali metal salt or alkaline earth metal salt thereof in the presence of dimethylformamide, thereby producing a mixture of a dichlorotolylsultone and a chlorosulfonylbenzoylchloride; (b) reacting the reaction products of step (a) with an alcohol having the formula ROH wherein R represents a lower alkyl group; (c) reacting the reaction product of step (b) with ammonia to form the ammonium salt of said 1.2-benzoisothiazole-3-on-1.1dioxide; and converting said ammonium salt to said 1.2-benzoisothiazole-3-on-1.1-dioxide.

2. The process according to claim 1, wherein the reaction of step (b) is conducted without separating the mixture of chlorosulfonylbenoylchloride and dichlorotolylsultone.

3. The process according to claim 1, wherein the reaction of the first step is conducted by adding phosgene in an inert solvent solution.

4. The process according to claim 1, wherein the reaction of step (a) is conducted by introducing phosgene into an inert solvent solution of the o-sulfobenzoic acid or an alkali metal salt or alkaline earth metal salt thereof.

5. The process according to claim 1, wherein the reaction mixture of step (a) is filtered and condensed and then the condensed reaction mixture is used in step (b).

6. The process according to claim 1, wherein an aqueous solution of ammonia is admixed with the reaction mixture of step (b).

7. The process according to claim 1, wherein ammonia gas is introduced into the reaction mixture of step (b).

8. The process according to claim 1, wherein the amount of said dimethylformamide is in the range of 0.01 to 0.3 mole per mole of the o-sulfobenzoic acid or the alkali metal salt or alkaline earth metal salt thereof.

9. The process according to claim 1, wherein the alkaline earth metal of said alkaline earth metal salt is magnesium, calcium or barium and the alkali metal of said alkali metal salt is sodium or potassium.

10. The process according to claim 3, wherein the inert solvent is an aliphatic hydrocarbon, a halohydrocarbon, an aromatic hydrocarbon, an ether, a ketone, a nitrile or an ester.

11. The process of claim 1, wherein said ammonium salt is converted by addition of a mineral acid.

* * * * *